United States Patent [19]

Bowley et al.

[11] Patent Number: 4,875,771

[45] Date of Patent: Oct. 24, 1989

[54] METHOD FOR ASSESSING DIAMOND QUALITY

[75] Inventors: Heather J. Bowley, Staines; Donald L. Gerrard, West Ewell, both of England

[73] Assignee: The British Petroleum Company p.l.c., London, United Kingdom

[21] Appl. No.: 91,065

[22] PCT Filed: Dec. 19, 1986

[86] PCT No.: PCT/GB86/00784

§ 371 Date: Aug. 6, 1987

§ 102(e) Date: Aug. 6, 1987

[87] PCT Pub. No.: WO87/03963

PCT Pub. Date: Jul. 2, 1987

[51] Int. Cl.⁴ .................. G01J 3/44; G01N 21/65; G01N 21/87

[52] U.S. Cl. .................................. 356/30; 356/301

[58] Field of Search .................. 356/301, 30

[56] References Cited

U.S. PATENT DOCUMENTS

| | | | |
|---|---|---|---|
| 3,414,354 | 12/1968 | Siegler, Jr. ........................ | 356/301 |
| 3,989,379 | 11/1976 | Eickhorst ........................... | 356/30 |
| 4,259,011 | 3/1981 | Crumm et al. ..................... | 356/30 |
| 4,394,580 | 7/1983 | Gielisse ............................. | 356/30 X |
| 4,397,556 | 8/1983 | Muller .............................. | 356/301 |
| 4,620,284 | 10/1986 | Schnell et al. .................. | 356/301 X |

FOREIGN PATENT DOCUMENTS

| | | |
|---|---|---|
| 643142 | 9/1928 | France . |
| 2496888 | 6/1982 | France . |
| 0158544 | 9/1982 | Japan ................................. 356/30 |
| 1384813 | 2/1975 | United Kingdom . |
| 1416568 | 12/1975 | United Kingdom . |
| 2010474 | 6/1979 | United Kingdom . |
| 0041348 | 12/1981 | United Kingdom ............... 356/30 |
| 2140555 | 11/1984 | United Kingdom ............ 356/301 |

OTHER PUBLICATIONS

S. A. Solin and K. A. Ramdas, Raman Spectrum of Diamond, Physical Review vol. 1, #4, pp. 1687–1698.

*Primary Examiner*—F. L. Evans
*Attorney, Agent, or Firm*—Morgan & Finnegan

[57] ABSTRACT

A method for assessing diamonds of differing quality characteristics in which a laser Raman spectrometer is initially calibrated by use of diamonds of known quality characteristics, the characteristics having been assessed for example by a conventional subjective procedure. Diamonds of unknown quality characteristic are successively placed in the spectrometer and irradiated with laser radiation of known frequency. The intensity of the scattered Raman signal from the diamond of unknown quality is monitored for one or more orientations of the diamond, the resultant signal being capable of relation to the quality of the diamond.

11 Claims, 1 Drawing Sheet

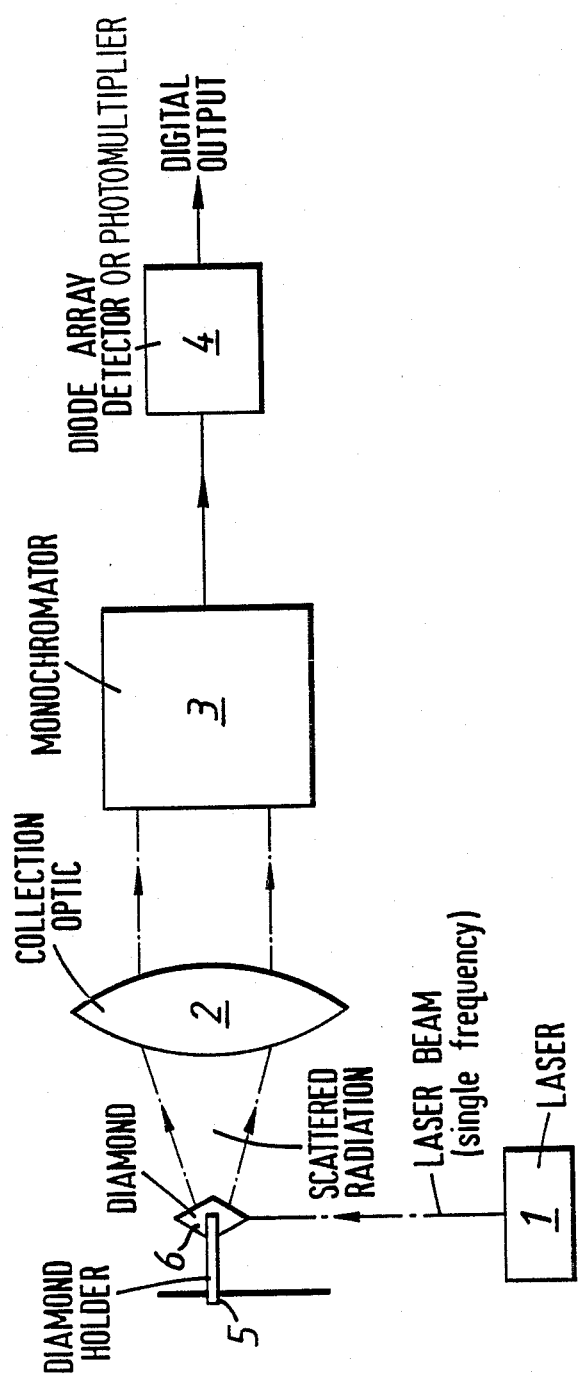

METHOD FOR ASSESSING DIAMOND QUALITY

The present invention relates to the assessment of diamond quality and more particularly relates to the assessment of diamond quality by means of Raman spectroscopic techniques.

The quality of valuable gems such as diamonds is generally determined in a subjective manner. Thus, a person allegedly expert in the art will examine the gem by eye and then express an opinion on the quality and value of the gem. However, it frequently occurs that the quality of the gem is differently judged by different persons. Also the procedure is slow, requires considerable skill and in view of its subjectively is not always consistent.

Laser Raman spectroscopy may be used for the separation of diamonds from a diamondiferous material and is disclosed in our co-pending GB patent application No. 2140555A. The method comprises the steps of passing discrete units of gangue through a beam of laser radiation capable of causing Raman spectral activation, detecting the scattered Raman radiation by means of a detector, the detector being adapted to actuate means for separating discrete units of diamond containing material from the discrete units of non-diamond containing material and collecting the separated discrete units.

The Raman signal of diamond is much stronger than that of other materials because diamond only contains C—C bonding and its Raman signal occurs at a position well separated from those of other minerals. Thus the Raman signal is highly specific for diamond. Also, because diamond only contains one type of C—C bond, there is only a single Raman signal which can be readily distinguished from associated broad band fluorescence.

It is an object of the present invention to provide means for effectively assessing the quality of a diamond in an objective manner so as to avoid resorting to subjective judgement by a human observer and it has now been found that laser Raman spectroscopy may be used as a basis for assessment or classifying diamonds of differing quality.

Thus according to the present invention there is provided a method for assessing diamonds of differing quality comprising the steps of (a) calibrating a laser Raman spectrometer with diamonds of known quality characteristics, (b) placing a diamond of unknown quality characteristic in a fixed orientation, (c) passing incident laser radiation of known frequency and intensity onto the diamond, and (d) monitoring the intensity of the scattered Raman signal for one or more orientations of the diamond of unknown quality characteristic.

It is preferred that the diamonds of differing quality are of a similar size range and thus it may be necessary to separate the diamonds into size ranges prior to using the method as hereinbefore described.

A laser Raman spectrometer adapted to emit a single frequency of radiation is calibrated by monitoring the intensity of the scattered Raman signal for a series of diamonds of known but differing quality. Preferably the diamonds of known but differing quality are of a single colour type e.g. white, yellow, green. The diamonds of known but differing quality may be assessed by conventional subjective means e.g. by use of an expert observer.

The diamonds used for calibration and those the quality of which are to be determined are mounted in a suitable holder and are assessed individually. Preferably the orientation of the diamonds with respect to the incident laser radiation is similar in each case but the method is not as sensitive to this requirement as certain other techniques.

The source of laser radiation is adapted to operate in a single frequency mode. The frequency of the radiation chosen is dependent on the colour type of the diamond being assessed.

The scattered Raman radiation from the diamond being assessed is filtered from other types of radiation by a suitable optical arrangement such as a collection optic and monochromator. A detector such as a photomultiplier or multichannel detector (e.g. diode array detector) may be used to detect the scattered Raman radiation, the intensity of the scattered radiation being capable of being related to the intensity of the colour and hence the quality of the diamond.

It is desirable prior to assessing the quality of an unknown diamond to determine whether or not the diamond contains internal crystal defects such as inclusions. Such defects may need to be taken into account when giving an assessment of diamond quality.

The present invention may be used for the assessment of both cut and uncut diamonds. Thus it is also envisaged that the above method may be adapted to a batch or continuous method of separating diamonds into portions of known quality from diamondiferous material. Thus, for example, the method of our co-pending UK patent application No. GB 2140555A may be used to sort diamonds from diamondiferous material, the resultant sorted diamonds then being separated into portions of known quality by the method as hereinbefore described.

Preferably the diamonds of unknown quality are of a single colour type e.g. white, yellow, green and it is preferred that the colour type of the diamonds is determined prior to assessment of their quality by a suitable method. The bulk of diamonds tend to be of white, yellow or green colour type and it is preferable to pre-classify the diamond colour type by a suitable technique before quality determination.

According to a further aspect of the invention there is provided an apparatus suitable for assessing diamond quality comprising (a) a source of laser radiation of known frequency, (b) means for holding a diamond in a fixed orientation so that it may be irradiated with the laser radiation, and (c) means for monitoring the scattered Raman radiation from the diamond. It is preferred that the means for monitoring the scattered Raman radiation comprises a photomultiplier or multichannel detector such as a diode array detector. Also the source of laser radiation may comprise an argon ion laser emitting radiation of a single frequency.

The invention will now be described by way of example only and with reference to the accompanying drawing.

The drawing is a schematic diagram of an apparatus for assessing diamond quality by means of laser Raman spectroscopy.

The apparatus has a source 1 of laser radiation operating in a single frequency mode i.e. only emitting a radiation of a single frequency. The frequency of the radiation chosen is dependent on the colour type of diamond being assessed. The laser used was a Spectra-Physics Model 2020 argon ion laser capable of output at 514.5 nm (nanometres). The laser was operated in its light mode at 50 mW thus maintaining constant photon flux.

The laser may be operated at different wavelengths if desired.

The analysis of the scattered laser radiation was carried out using an Anaspec 36 laser Raman spectrometer comprising a collection optic 2, a monochromator 3, a Reticon type S intensified diode array detector 4.

The diamond holder 5 was capable of supporting a diamond 6 in the light path of the laser radiation and was capable of varying the orientation of the diamond with respect to the direction of the laser radiation.

In use, the apparatus was calibrated with diamonds having known colour class ranging from 1 to 7. The colour types of the diamonds were yellow and green, class 1 being of the highest quality and class 7 being of the lowest quality, the qualities being determined by standard subjective assessment.

Each diamond was positioned in the holder 5 and located in the light path of the laser 1. The position of the diamond in the holder 5 was optimised to obtain the maximum signal for scattered Raman radiation at the detector. A measurement of the maximum Raman signal intensity was obtained for several orientations of each diamond. The intensity is expressed in number of photons counted per second. As the spread of these results was small in each case, a mean value of the intensity of the Raman signal for each diamond was calculated. The total accumulation time (the time taken to count the number of photons in the scattered Raman radiation) was of the order of one second and five diamonds in each class (where available) were examined. The accumulation time required is dependent on the frequency of the incident laser radiation and the diamond colour type.

The intensity of the Raman radiation is detected and measured by the diode array detector 4. Alternative detectors may be used, for example, a photomultiplier.

The results of the analyses of the diamonds of colour types yellow and green are given in Tables 1 and 2. Table 1 gives results for type yellow diamonds of classes 1 to 7 and Table 2 give results for type green diamonds of classes 1 to 6. The Raman intensities are given for five samples of diamonds (where possible) for each quality class and the value of the Raman intensity in the case of each stone is that calculated from five different orientations of the diamond in the holder. It was found that in each case the orientation of the diamond made little difference to the intensity of the Raman band due to its tetrahedral C—C stretching mode.

Examples of the spectra obtained for each colour class of diamond show that even in the "lowest" colour classes no significant background is detected. This appears to be advantageous as all of the signal at 1332 $cm^{-1}$ can be deemed as due to the Raman signal of the diamond with no contribution from fluorescence. Thus the technique may be used for assessment of diamonds having differences in their commercially accepted colour classes.

TABLE 1

Diamond Type - Yellow
Incident Radiation $\lambda_e$ —514.5 nm

| No. of Sample | Mean Radiation Intensity (counts/sec) | Quality Class |
|---|---|---|
| 1 | 200 613 | |
| 2 | 200 588 | |
| 3 | 200 492 | 1 |
| 4 | — | |
| 5 | — | |
| 1 | 160 490 | |
| 2 | 160 101 | |
| 3 | 159 376 | 2 |
| 4 | 158 954 | 2 |
| 5 | 158 627 | |
| 1 | 133 461 | |
| 2 | 133 450 | |
| 3 | 132 968 | 3 |
| 4 | 132 919 | |
| 5 | 132 888 | |
| 1 | 116 204 | |
| 2 | 116 201 | |
| 3 | 115 972 | 4 |
| 4 | 115 927 | |
| 5 | 115 883 | |
| 1 | 103 467 | |
| 2 | 102 978 | |
| 3 | — | 5 |
| 4 | — | |
| 5 | — | |
| 1 | 81005 | |
| 2 | 80834 | |
| 3 | 80609 | 6 |
| 4 | 80133 | |
| 5 | — | |
| 1 | 74958 | |
| 2 | — | |
| 3 | — | 7 |
| 4 | — | |
| 5 | — | |

TABLE 2

Diamond Type - Green
Incident Radiation $\lambda_e$ —514.5 nm

| No. of Samples | Mean Radiation Intensity (counts/sec) | Quality Class |
|---|---|---|
| 1 | 67355 | |
| 2 | 67326 | |
| 3 | 66839 | 1 |
| 4 | 65814 | |
| 5 | 65787 | |
| 1 | 49755 | |
| 2 | 49658 | |
| 3 | 49616 | 2 |
| 4 | 49383 | |
| 5 | 49072 | |
| 1 | 45301 | |
| 2 | 45273 | |
| 3 | 44796 | 3 |
| 4 | 44135 | |
| 5 | 43517 | |
| 1 | 41759 | |
| 2 | 40958 | |
| 3 | 40531 | 4 |
| 4 | 39467 | |
| 5 | 39401 | |
| 1 | 35289 | |
| 2 | 32705 | |
| 3 | 31642 | 5 |
| 4 | 27677 | |
| 5 | 23552 | |
| 1 | 14015 | |
| 2 | 3584 | |
| 3 | — | 6 |
| 4 | — | |
| 5 | — | |

We claim:

1. A method for assessing diamonds of differing quality comprising the steps:
   (a) calibrating a laser Raman spectrometer with diamonds of known quality characteristics, said spectrometer having a source of laser radiation, means for holding a diamond in a fixed orientation so that it may be irradiated with said radiation, and means for monitoring the intensity of scattered Raman radiation from said diamond, said calibration for each diamond of known quality characteristics comprising the steps: holding said diamond in a fixed orientation in said spectrometer, irradiating said diamond with laser radiation, and monitoring the intensity of scattered Raman radiation from said diamond, (b) holding a diamond of unknown quality characteristic in a fixed orientation in said spectrometer, (c) irradiating said diamond of unknown quality characteristics with laser radiation of known frequency and intensity from said source of laser radiation, (d) monitoring the intensity of scattered Raman radiation from said diamond of unknown quality characteristics for one or more orientations of said diamond, and (e) comparing the intensity of said scattered Raman radiation from said diamond of unknown quality characteristics with the intensities for said diamonds of known quality characteristics.

2. A method according to claim 1 in which the diamonds of unknown quality are separated, prior to assessment, into size ranges.

3. A method according to claim 1 or claim 2 in which the diamonds of unknown quality are of a single colour type.

4. A method according to claim 1, claim 2 in which the diamond of unknown quality characteristic is held in a fixed orientation by means of a holder, the holder being adapted to be capable of varying the orientation of the diamond with respect to the direction of the incident laser radiation.

5. A method according to claim 1 in which the source of laser radiation is adapted to provide incident radiation of a single frequency.

6. A method according to claim 1 in which the laser Raman spectrometer is calibrated with diamonds of known quality characteristics, the characteristics having been determined by a subjective method.

7. A method according to claim 1 in which the intensity of the scattered radiation is monitored by a multichannel detector.

8. A method according to claim 7 in which the multichannel detector comprises a diode array detector.

9. A method according to claim 1 in which the intensity of the scattered radiation is monitored by a photomultiplier.

10. A method according to claim 1 in which said scattered Raman radiation is filtered from other types of radiation by means adapted to pass only said scattered Raman radiation.

11. A method according to claim 10 in which said filter means comprises a collection optic and monochromator.

* * * * *